United States Patent
Powell

(10) Patent No.: US 10,045,925 B2
(45) Date of Patent: Aug. 14, 2018

(54) SKINCARE FORMULATIONS AND REGIMENS

(71) Applicant: Stella & Dot LLC, San Bruno, CA (US)

(72) Inventor: Christin Powell, San Bruno, CA (US)

(73) Assignee: STELLA & DOT LLC, Brisbane, CA (US)

( * ) Notice: Subject to any disclaimer, the term of this patent is extended or adjusted under 35 U.S.C. 154(b) by 0 days.

(21) Appl. No.: 14/931,744

(22) Filed: Nov. 3, 2015

(65) Prior Publication Data

US 2016/0120781 A1 May 5, 2016

Related U.S. Application Data

(60) Provisional application No. 62/074,536, filed on Nov. 3, 2014.

(51) Int. Cl.

| | |
|---|---|
| *A61K 8/49* | (2006.01) |
| *A61K 8/34* | (2006.01) |
| *A61K 8/97* | (2017.01) |
| *A61K 8/27* | (2006.01) |
| *A61K 8/29* | (2006.01) |
| *A61K 8/64* | (2006.01) |
| *A61Q 19/08* | (2006.01) |
| *A61K 8/73* | (2006.01) |
| *A61K 8/36* | (2006.01) |
| *A61Q 19/02* | (2006.01) |
| *A61Q 17/04* | (2006.01) |

(52) U.S. Cl.
CPC .............. *A61K 8/4953* (2013.01); *A61K 8/27* (2013.01); *A61K 8/29* (2013.01); *A61K 8/347* (2013.01); *A61K 8/361* (2013.01); *A61K 8/4946* (2013.01); *A61K 8/64* (2013.01); *A61K 8/735* (2013.01); *A61K 8/97* (2013.01); *A61Q 19/08* (2013.01); *A61Q 17/04* (2013.01); *A61Q 19/02* (2013.01)

(58) Field of Classification Search
CPC .................................................. A61K 8/4953
See application file for complete search history.

(56) References Cited

U.S. PATENT DOCUMENTS

| | | |
|---|---|---|
| 2005/0096256 A1 | 5/2005 | Sinclair |
| 2007/0065396 A1 | 3/2007 | Morariu |
| 2009/0042846 A1 | 2/2009 | Gupta |

FOREIGN PATENT DOCUMENTS

FR        2865398 A1        7/2005

OTHER PUBLICATIONS

International search report and written opinion dated Mar. 4, 2016 for PCT/US2015/058897.
Kang, et al. Wnt/β-catenin signaling mediates the antitumor activity of magnolol in colorectal cancer cells. Mol Pharmacol. Aug. 2012;82(2):168-77. doi:10.1124/mol.112.078535. Epub May 1, 2012.

*Primary Examiner* — Amber D Steele
(74) *Attorney, Agent, or Firm* — Wilson, Sonsini, Goodrich & Rosati

(57) ABSTRACT

Provided are compositions, comprising a neolignan, ectoin, and a molecule of Formula I:

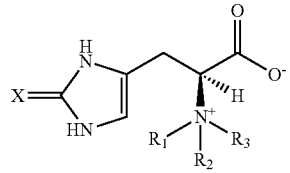

wherein $R_1$, $R_2$ and $R_3$ are independently H, methyl, ethyl, propyl, or isopropyl; wherein X is S or O. In some cases, the molecule of Formula I is ergothioneine (EGT). In some cases, the at least one neolignan is honokiol or a derivative thereof. Honokiol may be provided in the form of *magnolia* bark extract. Methods of making and using these compositions are also provided.

20 Claims, 10 Drawing Sheets

| Trade Name | INCI Name |
|---|---|
| Azeloglicina | Potassium Azeloyl Diglycinate |
| Witch hazel distillate | Hamamelis Virginiana (Witch Hazel) Extract |
| Nab Willow Bark Extract | Water (74%), Salix Nigra (Willow) Bark Extract (26%) |
| Lime Pearl | Glycerin (70%), Water (20-25%), Alcohol Denatured (5-10%), Microcitrus Australasica Fruit Extract (1-2%) |
| Sepitonic M3 | Magnesium Aspartate (4.5-5%), Zinc Gluconate (4.5-5%), Copper Gluconate (0.3-0.6%) |
| Actifraiste | Glycerin (45%), Water (20.18%), Mucor Miehei Extract (20%), Glucosamine HCl (12%), Urea (2.5%) |
| Thiotaine | Ergothioneine |
| Magnolia Essential Water M12385 | Magnolia Glauca Flower Water |
| LACTIC ACID 88% | Lactic Acid |
| Ectoin | Ectoin |
| MAXnolia | Maltodextrin (65%), Lecithin (29%), Water (5%), Magnolia Officinalis Bark Extract (0.45%), Tocopherol (0.3%), Vitis Vinifera (Grape) Seed Extract (0.09%) |

Figure 2 – Peel Pads

| Trade Name | INCI Name |
|---|---|
| Leuphasyl | Pentapeptide-18 |
| Argireline sol. liquid | Acetyl Hexapeptide-8 |
| Eyeliss | Water (77%), Glycerin (15%), Hesperidin Methyl Chalcone (5%), Steareth-20 (3%), Dipeptide-2 (0.1%), Palmitoyl Tetrapeptide-7 (330 ppm) |
| Eyeseryl Solution B | Water, Butylene Glycol, Acetyl Tetrapeptide-5 (0.1%) |
| Tetrahexyldecyl Ascorbate (BV-OSC) | Tetrahexyldecyl Ascorbate |
| Phospholipon 90G | Lecithin |
| Tocotrin 50 c | Elaeis Guineensis (Palm) Oil, Tocotrienols, Tocopherol |
| MAKnolia | Maltodextrin (86%), Lecithin (28%), Water (5%), Magnolia Officinalis Bark Extract (0.45%), Tocopherol (0.3%), Vitis Vinifera (Grape) Seed Extract (0.09%) |
| TYROSINE | Tyrosine |
| Ectoin | Ectoin |
| Thiotaine | L-Ergothioneine |
| ABS Songyi Mushroom Extract | Water, Tricholoma Matsutake Extract |

Figure 3 – Face & Eye Serum

| Trade Name | INCI Name |
|---|---|
| Sepitonic M3 | Magnesium Aspartate (4.5-5%), Zinc Gluconate (4.5-5%), Copper Gluconate (0.3-0.8%) |
| Phospholipon 90G | Lecithin |
| Thiotaine | L-Ergothioneine |
| Hyaluronic Filling Spheres | Ethylhexyl Palmitate, Silica Dimethyl Silylate, Butylene Glycol, Sodium Hyaluronate |
| Rita Avocado Oil | Persea Gratissima (Avocado) Oil |
| Tetrahexyldecyl Ascorbate (BV-OSC) | Tetrahexyldecyl Ascorbate |
| Squalane | Squalane |
| Evening primrose oil | Oenothera Biennis (Evening Primrose) Oil |
| Ectoin | Ectoin |
| MAXnolia | Maltodextrin (66%), Lecithin (29%), Water (5%), Magnolia Officinalis Bark Extract (0.45%), Tocopherol (0.3%), Vitis Vinifera (Grape) Seed Extract (0.09%) |
| ALOE VERA GEL 200:1 CONC. | Aloe Barbadensis Leaf Juice |
| Macadamia Nut Oil | Macadamia Ternifolia Seed Oil |
| Tocomin 50 c | Elaeis Guineensis (Palm) Oil, Tocotrienols, Tocopherol |
| ABS Songyi Mushroom Extract | Water, Tricholoma Matsutake Extract |

Figure 4 – Moisture injection cream

| Trade name | INCI name |
|---|---|
| ZinClear IM 50CCT | Zinc Oxide |
| | Caprylic/Capric Triglyceride |
| | Glyceryl Isostearate |
| | Polyhydroxystearic Acid |
| Thiotaine | Ergothioneine |
| | Water |
| Bont-L Peptide Solution | Palmitoyl Hexapeptide-19 |
| | Phenoxyethanol |
| BV-OSC | Tetrahexyldecyl Ascorbate |
| Ectoin | Ectoin |
| | Ethylhexyl Palmitate |
| Hyaluronic FS | Silica Dimethyl Silylate |
| | Butylene Glycol |
| | Pentylene Glycol |
| | Sodium Hyaluronate |
| MAXnolia | Maltodextrin |
| | Lecithin |
| | Water |
| | Magnolia Officinalis Bark Extract |
| | Tocopherol |
| | Vitis Vinifera (Grape) Seed Extract |

Figure 5 – Moisturizer Broad Spectrum SPF 20

| Trade name | INCI name |
|---|---|
| Titanium Dioxide | Titanium Dioxide |
| | Zinc Oxide |
| ZinClear IM 50CCT | Capric/Caprylic Triglyceride |
| | Glyceryl Isostearate |
| | Polyhydroxystearic Acid |
| Thiotaine | Ergothioneine |
| Renovage | Capric/Caprylic Triglyceride |
| | Teprenone |
| BV-OSC | Tetrahexyldecyl Ascorbate |
| Ectoin | Ectoin |
| | Ethylhexyl Palmitate |
| Hyaluronic FS | Silica Dimethyl Silylate |
| | Butylene Glycol |
| | Pentylene Glycol |
| | Sodium Hyaluronate |
| MAXnolia | Maltodextrin |
| | Lecithin |
| | Water |
| | Magnolia Officinalis Bark Extract |
| | Tocopherol |
| | Vitis Vinifera (Grape) Seed Extract |

Figure 6 – Tinted Moisturizer Broad Spectrum SPF 32

| Trade Name | INCI Name |
|---|---|
| Bressine | Water, Plankton Extract |
| Ultra Filling Spheres | Ethylhexyl Palmitate, Trihydroxystearin, Sodium Hyaluronate, Amorphophallus Konjac Root Powder |
| Biodynes TRF | Saccharomyces Lysate Extract |
| Pinoxide | Butylene Glycol (96-98%), Pinanediol (1-2%), Camphanediol (1-2%) |
| Caffeine anhydrous USP | Caffeine |
| VITAMIN E LIQUID (1350) | Tocopheryl Acetate |
| Allantoin | Allantoin |
| Ectoin | Ectoin |
| Tetrahexyldecyl Ascorbate (BV-OSC) | Tetrahexyldecyl Ascorbate |
| Thiotaine | Ergothioneine |
| MAXnolia | Maltodextrin (65%), Lecithin (29%), Water (5%), Magnolia Officinalis Bark Extract (0.45%), Tocopherol (0.3%), Vitis Vinifera (Grape) Seed Extract (0.09%) |

Figure 7 – Eye Lift

Figure 9

Moisturizing Cream

Active Ingredients:

| Components | INCI Name |
|---|---|
| Component 1 | Glycerin (37-42%), Water(31-38%), Sodium PCA (5-11%), Urea (5-11%), Trehalose (1-4%), Triacetin (0.3-0.6%), Polyquaternium-51 (0.1-1%), Sodium Hyaluronate (0.05-0.1%) |
| Component 2 | Magnesium Aspartate (4.5-5%), Zinc Gluconate (4.5-5%), Copper Gluconate (0.3-0.8%) |
| Component 3 | Lecithin |
| Component 4 | Ergothioneine |
| Component 5 | Ethylhexyl Palmitate, Silica Dimethyl Silylate, Butylene Glycol, Sodium Hyaluronate |
| Component 6 | Glycerin (50%), Water, Methylglucoside Phosphate (4.5-5.5%), Copper Lysinate/Prolinate (1-5%) |
| Component 7 | Panthenol |
| Component 8 | Ethyl Linoleate |
| Component 9 | Persea Gratissima (Avocado) Oil |
| Component 10 | Tetrahexyldecyl Ascorbate |
| Component 11 | Squalane |
| Component 12 | Oenothera Biennis (Evening Primrose) Oil |
| Component 13 | Fragrance |
| Component 14 | Allantoin |
| Component 15 | Stearyl Glycyrrhetinate |
| Component 16 | Ectoin |
| Component 17 | Maltodextrin (66%), Lecithin (29%), Water (5%), Magnolia Officinalis Bark Extract (0.45%), Tocopherol (0.3%), Vitis Vinifera (Grape) Seed Extract (0.09%) |
| Component 18 | Macadamia Ternifolia Seed Oil |
| Component 19 | Water, Tricholoma Matsutake Extract |

Figure 10: Cream

| Components | INCI Name |
|---|---|
| Component 1 | Water |
| Component 2 | Caprylic/Capric Triglyceride |
| Component 3 | Ricinus Communis (Castor) Seed Oil (74-95%), Hydrogenated Castor Oil (5-15%), Cera Alba (2-6%), Copernicia Cerifera (Carnauba) Wax (1-2%) |
| Component 4 | Cetearyl Olivate (50-70%), Sorbitan Olivate (30-50%) |
| Component 5 | Glycerin (37-42%), Water(31-38%), Sodium PCA (5-11%), Urea (5-11%), Trehalose (1-4%), Triacetin (0.3-0.6%), Polyquaternium-51 (0.1-1%), Sodium Hyaluronate (0.05-0.1%) |
| Component 6 | Cetearyl Alcohol (70-80%), Ceteareth-20 (20-30%) |
| Component 7 | Lecithin |
| Component 8 | Glycerin |
| Component 9 | Dimethicone |
| Component 10 | Ergothioneine |
| Component 11 | Isosorbide Dicaprylate |
| Component 12 | Ethylhexyl Palmitate(95.3%), Silica Dimethyl Silylate (2.5%), Butylene Glycol (1%), Pentylene Glycol (1%) Sodium Hyaluronate (.2%) |
| Component 13 | Magnesium Aluminum Silicate |
| Component 14 | Panthenol |
| Component 15 | Phenoxyethanol (88.5-91.5%), Ethylhexylglycerin (8.5-11.5%) |
| Component 16 | Glyceryl Behenate |
| Component 17 | C8-22 Alkyl Acrylates/Methacrylic Acid Crosspolymer |
| Component 18 | Glycerin (50%), Water, Methylglucoside Phosphate (4.5-5.5%), Copper Lysinate/Prolinate (1-5%) |
| Component 19 | Fragrance |
| Component 20 | Tetrahexyldecyl Ascorbate |
| Component 21 | Squalane |
| Component 22 | Oenothera Biennis (Evening Primrose) Oil |
| Component 23 | Citric Acid |
| Component 24 | Xanthan Gum |
| Component 25 | Allantoin |
| Component 26 | Stearyl Glycyrrhetinate |
| Component 27 | Ectoin |
| Component 28 | Maltodextrin (66%), Lecithin (29%), Water (5%), Magnolia Officinalis Bark Extract (0.45%), Tocopherol (0.3%), Vitis Vinifera (Grape) Seed Extract (0.09%) |
| Component 29 | Aloe Barbadensis Leaf Extract |
| Component 30 | Macadamia Ternifolia Seed Oil |
| Component 31 | Magnesium Aspartate (4.5-5%), Zinc Gluconate (4.5-5%), Copper Gluconate (0.3-0.8%) |
| Component 32 | Persea Gratissima (Avocado) Oil |
| Component 33 | Ethyl Linoleate |
| Component 34 | Sodium Phytate |
| Component 35 | Water (79.4%), Tricholoma Matsutake Extract (20%) |

SEQUENCE LISTING

```
<160> NUMBER OF SEQ ID NOS: 7

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Glu Met Gln Arg Arg
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gln Pro Arg
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 3

Ala His Ser His
1

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac; C-term CONH2

<400> SEQUENCE: 4

Glu Glu Met Gln Arg Arg
1               5

<210> SEQ ID NO 5
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Beta-Ala

<400> SEQUENCE: 5

Ala His Ser His
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac; C-term OH
<220> FEATURE:
<221> NAME/KEY: MOD_RES
<222> LOCATION: (1)..(1)
<223> OTHER INFORMATION: Beta-Ala

<400> SEQUENCE: 6

Ala His Ser His
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Palmitoyl

<400> SEQUENCE: 7

Gly Gln Pro Arg
1
```

SKINCARE FORMULATIONS AND REGIMENS

CROSS-REFERENCE

This application claims the benefit under 35 U.S.C. § 119(e) of U.S. Provisional Patent Application No. 62/074,536, filed Nov. 3, 2014, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Mar. 6, 2017, is named 46631-702 201 SL.txt and is 1,905 bytes in size.

BACKGROUND

Skin changes are one of the most prominent signs of aging. Throughout aging, the skin can develop lines and wrinkles, undergo a loss of elasticity, develop spots and pigmentation, redden due to an increase in capillary appearance, lose radiance, roughen, develop an uneven tone, dry, thin, and/or become sallow. Further, acute and chronic inflammation as well as Reactive Oxygen Species (ROS) can lead to skin cell degradation and ultimately cell death, which can contribute to the signs of skin aging. Changes to the skin can begin in the mid to late 20's and can both result in injury or disease and be cosmetically undesirable. Accordingly, a skincare formulation and regimen that can slow the aging of skin and/or help reduce the visible signs of aging is needed.

SUMMARY OF THE DISCLOSURE

Provided is a composition comprising: at least one neolignan, ectoin, and a molecule of Formula I:

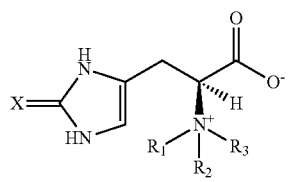

wherein $R_1$, $R_2$ and $R_3$ are independently H, methyl, ethyl, propyl, or isopropyl; wherein X is S or O. In some embodiments, when said composition is contacted with a skin cell in a predetermined amount for a predetermined period of time the result is a reduction of at least one symptom of skin aging. In some cases, is the molecule of Formula I, wherein X is S. In some cases, $R_1$, $R_2$ and $R_3$ are methyl. In some cases, the molecule of Formula I is ergothioneine (EGT). In some cases, the at least one neolignan is honokiol or a derivative thereof. Honokiol may be provided in the form of *magnolia* bark extract.

In certain embodiments are provided compositions described herein, comprising about 0.01% w/w-25% w/w neolignan, 0.1% w/w-70% w/w molecule of Formula I, and 0.1 w/w-25% w/w ectoin based on the total weight of the composition; wherein said molecule of Formula I is:

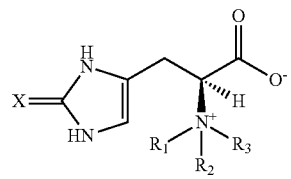

wherein $R_1$, $R_2$ and $R_3$ are independently H, methyl, ethyl, propyl, or isopropyl; wherein X is S or O. In some cases, in the molecule of Formula I, X is S. In some cases, $R_1$, $R_2$ and $R_3$ are methyl. In some cases, the molecule of Formula I is ergothioneine (EGT).

Provided is a composition for cosmetic use comprising: at least one neolignan; at least one neuropeptide; and a molecule of Formula I:

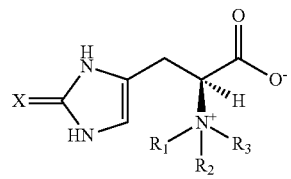

wherein $R_1$, $R_2$ and $R_3$ are independently H, methyl, ethyl, propyl, or isopropyl; wherein X is S or O. In some cases, in the molecule of Formula I, X is S. In some cases, $R_1$, $R_2$ and $R_3$ are methyl. In some cases, the molecule of Formula I is ergothioneine (EGT). In some cases, the at least one neolignan is honokiol. In some cases, the neuropeptide comprises the sequence: Tyr-D-Ala-Gly-Phe-Leu, or the sequence Glu-Glu-Met-Gln-Arg-Arg (SEQ ID NO: 1).

Also provided is a composition for cosmetic use, comprising sergothioneine; honokiol; ectoin; a first polypeptide comprising the sequence Tyr-D-Ala-Gly-Phe-Leu (pentapeptide-18) or a derivative thereof; a second polypeptide comprising the sequence Ac-Glu-Glu-Met-Gln-Arg- Arg-CONH2(Acetyl Hexapeptide-8) (SEQ ID NO: 4) or a derivative thereof; a third polypeptide comprising a palmitic acid conjugate of a polypeptide comprising the sequence Gly-Gln-Pro-Arg (Palmitoyl Tetrapeptide-7) (SEQ ID NO: 2) or a derivative thereof; and a fourth polypeptide comprising the sequence Ac-beta-Ala-His-Ser-His (Acetyl Tetrapeptide-5) (SEQ ID NO: 5) or a derivative thereof.

In one embodiment, a formulation to help reduce the visible signs of skin aging includes *magnolia* bark extract, ergothioneine, and ectoin.

This and other embodiments can include one or more of the following features. The formulation can include 15-25% *magnolia* bark extract, 50-70% ergothioneine, and 15-25% ectoin based on the total weight of the composition. The *magnolia* bark extract can be in liposomal form. The formulation can be part of a cream or pad. The cream or pad further can further include Vitamin C Ester, Peptide Blends, Alpha Hydroxy and Beta Hydroxy Acids, Hyaluronic Acid, Mushroom Ferment Extract, Multi-mineral Blends (Copper-Magnesium-Zinc), Phospholipids (for instance Lecithin), Caffeine, and/or Micro-Algae Blends.

Also provided herein is a composition for cosmetic use comprising: at least one neolignan; at least one ultraviolet spectrum attenuating agent comprising a plurality of nanoparticles or microparticles; and a molecule of Formula I:

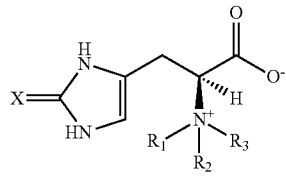

wherein $R_1$, $R_2$ and $R_3$ are independently H, methyl, ethyl, propyl, or isopropyl; wherein X is S or O. In some cases, in the molecule of Formula I, X is S. In some cases, $R_1$, $R_2$ and $R_3$ are methyl. In some cases, the molecule of Formula I is ergothioneine (EGT). The neolignan may be honokiol. In some cases, the at least one ultraviolet spectrum attenuating agent comprises zinc oxide, titanium dioxide, combinations or derivatives thereof. The composition may also comprise a plurality of hyaluronic microspheres.

In one embodiment, a method of reducing the visible signs of skin aging includes at least one of: (1) cleansing the skin; (2) exfoliating the skin with an exfoliating formulation; (3) treating the skin with a treatment formulation; and (4) moisturizing the skin with a moisturizing formulation. The exfoliating formulation, the treatment formulation, or the moisturizing formulation includes *magnolia* bark extract, ergothioneine, and ectoin.

These and other embodiments can include one of at least one of: (1) cleansing the skin; (2) exfoliating the skin with an exfoliating formulation; (3) treating the skin with a treatment formulation; and (4) moisturizing the skin with a moisturizing formulation. The method can further include repeating the steps twice daily. The method can further include repeating the steps for 30 days.

BRIEF DESCRIPTION OF THE DRAWINGS

Novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 2 is a table showing ingredients of a peel pad.

FIG. 3 is a table showing ingredients of a face and eye serum.

FIG. 4 is a table showing ingredients of a moisture injection cream.

FIG. 5 is a table showing ingredients of a moisturizer with SPF 20.

FIG. 6 is a table showing ingredients of a moisturizer with SPF 32.

FIG. 7 is a table showing ingredients of an eye lift product.

FIG. 9 is a table showing ingredients of a composition described herein.

FIG. 10 is a table showing ingredients of a composition described herein.

Figure 1:
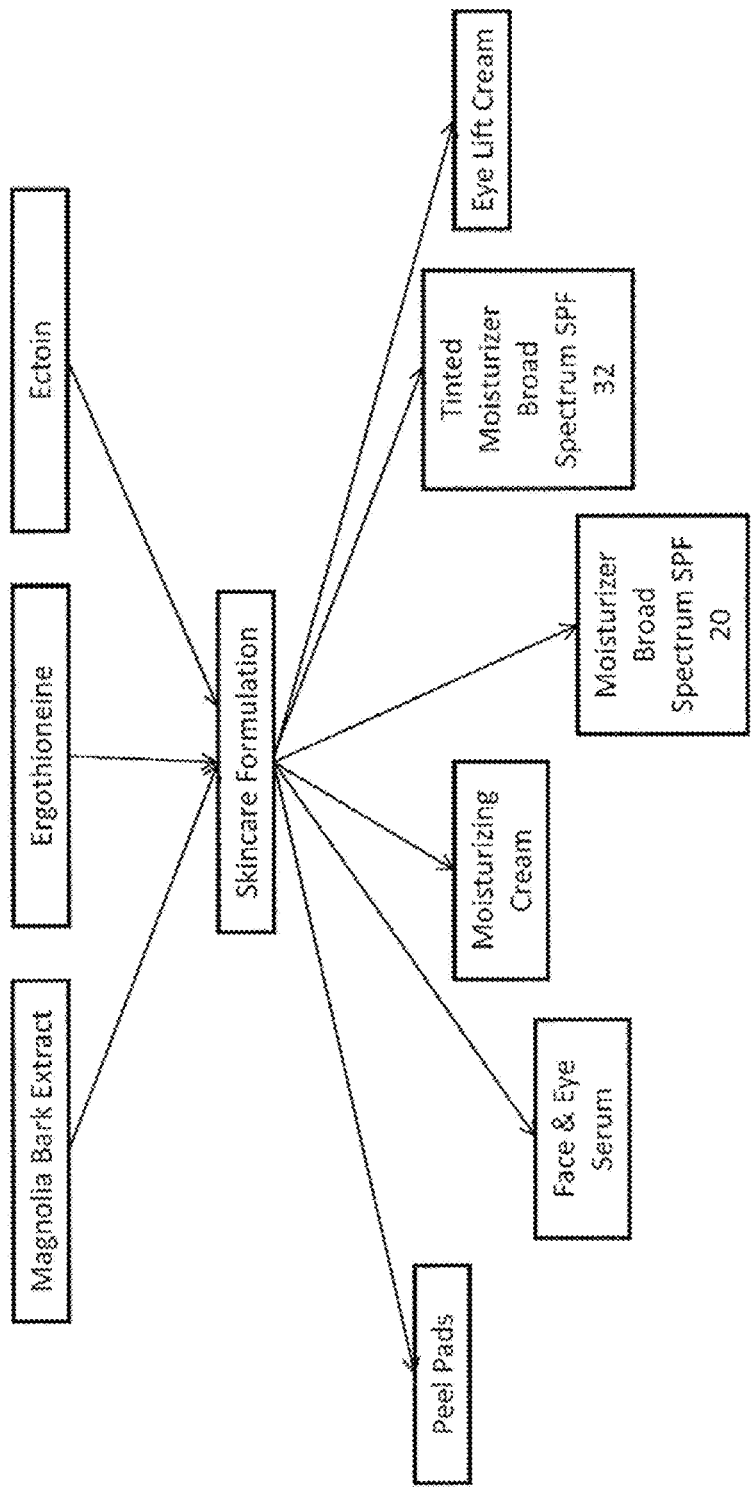
FIG. 1 is a chart showing ingredients and uses of a skincare composition.

In the Figures when percentages are provided, the percentages are w/w based on either total weight of the composition, or total weight of a multi-component ingredient, which can be discerned by reviewing the Figure.

DETAILED DESCRIPTION

Described herein is a topical formulation and method of use for helping to reduce visible signs of aging in a population.

Provided is a composition comprising: at least one neolignan, ectoin, and a molecule of Formula I:

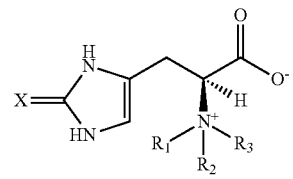

wherein $R_1$, $R_2$ and $R_3$ are independently H, methyl, ethyl, propyl, or isopropyl; wherein X is S or O. In some cases, when said composition is contacted with a skin cell in a predetermined amount for a predetermined period of time, the contacting results in a reduction of at least one symptom of skin aging. In some cases, in the molecule of Formula I, X is S. In some cases, $R_1$, $R_2$ and $R_3$ are methyl. In some cases, the molecule of Formula I is ergothioneine (EGT). In some cases, the at least one neolignan is honokiol or a derivative thereof. Honokiol may be provided in the form of *magnolia* bark extract.

The *magnolia* bark extract can be extracted from the *Magnolia* plant belonging to the China pharmacopoeia. Further, the *magnolia* bark extract can include two pharmacologically active substances, magnolol and honokiol. Magnolol can be represented by the following chemical formula:

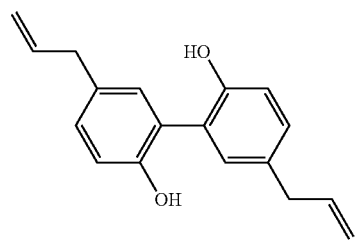 [SMILES: C=CCc1ccc(O)c(-c2cc(CC=C)ccc2O)c1]

Likewise, honokiol can be represented by the following chemical formula:

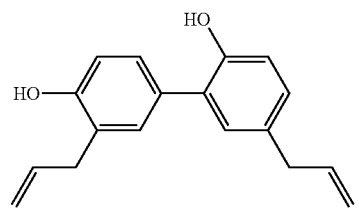 [SMILES: C=CCc1ccc(O)c(-c2ccc(O)c(CC=C)c2)c1]

The honokiol and magnolol can work synergistically to help reduce visible inflammation by e.g. inhibiting protein complex NF-KB activation and activity through IKK (IKB kinase) enzyme inactivation. They can also inhibit the production of inducible nitric oxide synthase (iNOS), interleukin 8 (IL-8), tumor necrosis factor α (TNF-α), and/or cyclooxygenase-2 (COX-2). In some embodiments, the *magnolia* bark extract can be included in the formulation in a liposomal form, e.g., with Lecithin as a carrier, which can advantageously allow the *magnolia* bark extract to dissolve within the lipids of the skin. Further, in some embodiments, the *magnolia* bark extract can be provided as part of a larger *magnolia* mixture that includes *magnolia* bark extract, maltodextrin, lecithin, water, tocopherol, and grape seed extract for e.g. delivery and/or preservation.

Compositions described herein may contain at least one molecule of Formula I. In some cases, the molecule of Formula I is ergothioneine (EGT). The EGT within the compositions described herein can be represented by the following chemical formula:

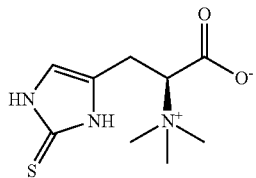

The EGT can advantageously act as an antioxidant to scavenge free radicals and prolong cell activity and youthfulness of skin. The EGT can also advantageously recycle Vitamin C, which is an antioxidant that can reduce the extent of scarring and/or wrinkles of the skin.

Some compositions described herein may contain ectoin. In some cases, ectoin can be extracted from a halophilic bacteria called *Halomonus Elongata*, wherein ectoin compensates osmotic pressure in bacteria and stabilizes biopolymers to protect the bacteria against dehydration, high temperature, and UV-damage. The ectoin can be represented by the following formula:

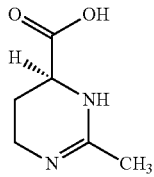

The ectoin can advantageously protect the skin from high temperatures, chemicals, surfactants, allergens, UV radiation, and dehydration. The ectoin can further act as a natural immune protector and support the skin's natural physiology.

The *magnolia* bark extract, ergothioneine, and ectoin can advantageously work synergistically via molecular markers to send messages to skin cells to help reduce visible inflammation, increase hydration, and support cell DNA, all key functions of maintaining healthy, youthful skin. All three ingredients can target the same molecular markers (hydration) and contribute to anti-inflammatory effects and fight free radicals, helping to prevent the breakdown of cell function and protecting against environmental and lifestyle stress factors.

In some embodiments, the compositions can include 10-30% w/w, such as 15-25% w/w, such as approximately 20% w/w ectoin; 40-80% w/w, such as 50-70% w/w, such as 55-65% w/w, such as approximately 60% w/w EGT; and 10-30% w/w, such as 15-25% w/w, such as approximately 20% w/w *magnolia* bark extract based on the total weight of the composition. Further in some embodiments, the skincare formulation can be used as part of one or more skincare products, such as creams or pads. For example, as shown in FIG. 1, the skincare formulation can be used as part of a peel pad, a face and eye serum, a moisturizing cream with or without SPF 20, and/or an eye lift cream.

Exemplary compositions described herein are shown in FIGS. 2-7, 9-10. For example, the peel pad product shown in FIG. 2 can include various acids such as azelaic, lactic and salicylic acid (e.g., in the form of willow bark extract) that exfoliate, smooth the skin and help stimulate collagen, and the formulation of *magnolia* bark extract, ectoin, and ergothioneine. Further, the face and eye serum product shown in FIG. 3 can include Vitamin C, and/or one or more of four different peptides which can achieve at least one of the following: help smooth and fill wrinkles, tighten the skin, reduce dark circles and puffiness, and even out skin tone. The four different peptides can be selected from the peptides described herein. The moisturizing cream of FIG. 4 can include phospholipids, hyaluronic filling spheres, and an advanced moisture complex to achieve at least one of: hydrate, moisturize and help fill visible lines and wrinkles. Likewise, the moisturizing cream of FIG. 5 can include a peptide described herein, Vitamin C, and micronized zinc oxide to help stimulate collagen and elastin, brighten skin tone and provide UVA/UVB protection with a non-chalky appearance. The moisturizing cream of FIG. 6 can include teprenone, Vitamin C, and micronized zinc oxide to help repair skin cell DNA, stimulate collagen and elastin and provide UVA/UVB protection with a non-chalky appearance. The eye lift cream of FIG. 7 can include pinanediol, microalgae, Vitamin C, and caffeine to help achieve at least one of: help reduce the appearance of dark circles, firm and lift, brighten and improve circulation around the eye area.

The skincare formulation and products can be used as part of a regimen to help reduce the visible signs of aging. For example, referring to FIG. 8, the user can do at least one of the following: cleanse the skin to remove makeup, dirt, and oil; exfoliate the skin to remove the superficial layer of dead skin cells on the surface and promote the skin's natural ability to produce new collagen. A product including the skincare formulation described herein can be used to exfoliate, e.g., the peel pad described with respect to FIG. 2, such as a peel pad made from 100% cotton, cotton blends comprising about 10%, about 20%, about 30%, about 40%, about 50%, about 60%, about 70%, about 80%, or about 90% cotton, or synthetic materials. The user can treat the skin by depositing potent antioxidants, peptides, and collagen-stimulators into the skin. Such treatment can be performed, for example, with a face and eye serum such as the serum described with respect to FIG. 3. Advantageously, by applying the treatment product after exfoliation, the pores will be open so that the ingredients (such as the *magnolia* bark extract, ectoin, ergothioneine, Vitamin C and/or one or more peptides described herein) can easily penetrate the skin. Finally, the user can moisturize and protect the skin. For example, the moisturizing creams of FIG. 4, 5, or 6 can be used.

In some embodiments, the eye lift cream of FIG. 7 can be used as desired to help firm and support circulation and reduce puffy eyes.

Figure 8:
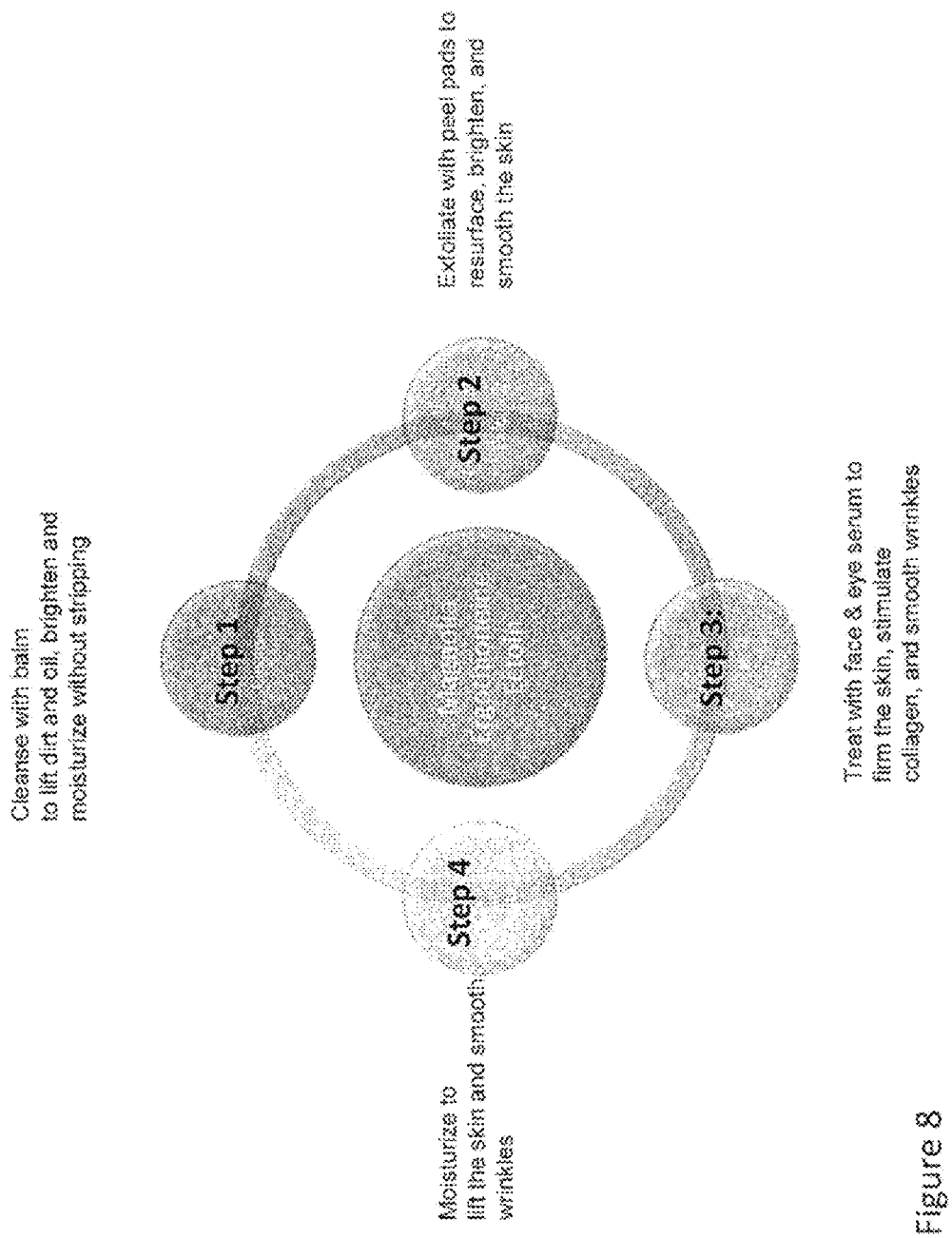
FIG. 8 is a flow chart for skin treatment.

Two independent studies on 40 women and 1 man ages 35-55 were performed using the steps shown in FIG. 8 twice daily for 30 days. More than 50% of the individuals experienced a decrease in one or more visible signs of aging.

Reference to a singular item, includes the possibility that there are a plurality of the same items present. More specifically, as used herein and in the appended claims, the singular "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

Provided is a composition comprising: at least one neolignan, at least one molecule of Formula I and ectoin, in an amount sufficient to result in a reduction of at least one symptom of skin aging when said composition is provided to a skin cell in a predetermined amount for a predetermined period of time. In some cases, the molecule of Formula I is ergothioneine (EGT). In some cases, the at least one neolignan is honokiol or a derivative thereof. Honokiol may be provided in the form of *magnolia* bark extract.

In some embodiments, the reduction of least one symptom of skin aging may be an improvement in the appearance of skin hyperpigmentation, a reduction in the appearance of crow's feet, an improvement in the elasticity of the skin, an improvement in the firmness or texture of the skin, and/or a reduction in the appearance of redness of the skin.

In certain embodiments, the predetermined period of time is from about one day to about 24 weeks, or about 6 weeks, or at least about 4 weeks.

In some embodiments, a composition provided herein may also comprise at least one ultraviolet spectrum attenuating agent in an amount sufficient to reduce the exposure of said skin cell from ultraviolet radiation as compared to an otherwise identical composition not comprising said ultraviolet spectrum attenuating agent.

In some cases, the at least one ultraviolet spectrum attenuating agent comprises a plurality of nanoparticles. A nanoparticle as defined herein may include a microscopic particle of matter that is measured on the nanoscale, e.g. one that measures less than 1000 nanometers, less than 500 nanometers or less than 100 nanometers. In some cases, the nanoparticles measure from about 1 to about 50 nanometers. In some cases, the nanoparticles measure from about 0.5 to about 50 nanometers in diameter. In some cases, the nanoparticles measure from about 1 to about 80 nanometers in diameter. In some cases, the nanoparticles measure from about 10 to about 100 nanometers. In some cases 5% by weight of the ultraviolet spectrum attenuating agent is present as nanoparticles based on the total weight of the ultraviolet spectrum attenuating agent. In some cases up to 10%, 20%, 25%, 30%, 35%, 40%, 45%, 50%, 55%, 60%, 65%, 70%, 75%, 80%, 85%, 90%, 95% or 100% by weight of the ultraviolet spectrum attenuating agent is present as nanoparticles based on the total weight of the ultraviolet spectrum attenuating agent.

The at least one ultraviolet spectrum attenuating agent comprises a plurality of microparticles. A microparticle as defined herein may include a particle of matter that is measured on the microscale, e.g. one that measures from about 0.1 to about 1000 micrometers. In some cases, the microparticles measure less than 500 micrometers, less than 400 micrometers, less than 300 micrometers, less than 200 micrometers, less than 100 micrometers or less than 50 micrometers. In some cases, the microparticles measure from about 1 to about 50 nanometers. In some cases, the microparticles measure from about 0.1 to about 100 micrometers in diameter. In some cases, the microparticles measure from about 1 to about 100 micrometers in diameter. In some cases, the microparticles measure from about 10 to about 100 micrometers. In some cases 5% by weight of the ultraviolet spectrum attenuating agent is present as microparticles based on the total weight of the ultraviolet spectrum attenuating agent. In some cases up to 10%, 20%, 25%, 30%, 35%, 40%, 45%, 50%, 55%, 60%, 65%, 70%, 75%, 80%, 85%, 90%, 95% or 100% by weight of the ultraviolet spectrum attenuating agent is present as microparticles based on the total weight of the ultraviolet spectrum attenuating agent The at least one ultraviolet spectrum attenuating agent may comprise zinc oxide, titanium dioxide, derivatives or combinations thereof.

In some cases, a composition provided herein may also comprise zinc oxide and titanium dioxide. In some embodiments, a composition provided herein comprises from about 1% w/w to about 20% w/w zinc oxide and from about 05% w/w to about 20% w/w titanium dioxide, based on the total weight of the composition. In some cases, a composition provided herein comprises about 6% w/w zinc oxide and about 4.5% w/w titanium dioxide, based on the total weight of the composition.

In some cases, a composition provided herein may further comprise at least one polypeptide, derivative or fragment thereof, or protein, derivative or fragment thereof. The at least one polypeptide may be a neuropeptide. In some cases, the neuropeptide is a pentapeptide that binds to an enkephelin receptor. In a few cases, the polypeptide comprises the sequence: Tyr-D-Ala-Gly-Phe-Leu. In some cases, the neuropeptide is a synaptosomal associated protein-25(SNAP-25) or a fragment or variant thereof. The fragment of SNAP-25may comprise a hexapeptide. In some cases, the hexapeptide has a sequence comprising Glu-Glu-Met-Gln-Arg- Arg (SEQ ID NO: 1). In select cases the hexapeptide is Ac-Glu-Glu-Met-Gln-Arg-Arg-CONH$_2$ (SEQ ID NO: 4).

In some embodiments, a composition provided herein may further comprise at least one polypeptide, protein, or derivative or fragment thereof, wherein the at least one polypeptide is conjugated to a fatty acid. The fatty acid may be a saturated fatty acid. In some cases, the saturated fatty acid is selected from propionic acid, butyric acid, valeric acid, caproic acid, enanthic acid, caprylic acid, pelargonic acid. capric acid, undecylic acid, lauric acid, tridecylic acid, myristic acid, pentadecylic acid, palmitic acid, margaric acid, stearic acid, nonadecylic acid and arachidic acid. In some embodiments, the composition may comprise a palmitic acid conjugate of a polypeptide comprising the sequence Gly-Gln-Pro-Arg (Pal-Gly-Gln-Pro-Arg) (SEQ ID NOS 2and 7, respectively).

In some embodiments, a composition provided herein may further comprise at least one polypeptide, protein, or derivative or fragment thereof, wherein the at least one polypeptide comprises the sequence beta-Ala-His-Ser-His (SEQ ID NO: 3), or derivative thereof In some cases, the at least one polypeptide comprises Ac-beta-Ala-His-Ser-His-OH (SEQ ID NO: 6).

In some embodiments are compositions described herein, further comprising: a first polypeptide comprising the sequence Tyr-D-Ala-Gly-Phe-Leu (Pentapeptied-18) or a derivative thereof; a second polypeptide comprising the sequence Ac-Glu-Glu-Met-Gln-Arg-Arg-CONH$_2$ (Acetyl Hexapeptide-8) (SEQ ID NO: 4) or a derivative thereof; a third polypeptide comprising a palmitic acid conjugate of a polypeptide comprising the sequence Gly-Gln-Pro-Arg (Palmitoyl Tetrapeptide-7) (SEQ ID NO: 2) or a derivative thereof; and a fourth polypeptide comprising the sequence Ac-beta-Ala-His-Ser-His (Acetyl Tetrapeptide-5) (SEQ ID NO: 5) or a derivation thereof.

In certain embodiments are provided compositions described herein, comprising about 0.01% w/w-25% w/w neolignan, 0.1% w/w-70% w/w molecule of Formula I, and 0.1 w/w-25% w/w ectoin, based on the total weight of the composition.

In certain embodiments is provided a composition for cosmetic use comprising: at least one neolignan; at least one molecule of Formula I; and at least one neuropeptide. In some cases, the molecule of Formula I is ergothioneine. In some cases, the at least one neolignan is honokiol. In some cases, the neuropeptide comprises the sequence: Tyr-D-Ala-Gly-Phe-Leu, or the sequence Glu-Glu-Met-Gln-Arg-Arg (SEQ ID NO: 1).

In certain embodiments is provided a composition for cosmetic use, comprising ergothioneine; honokiol; ectoin; a first polypeptide comprising the sequence Tyr-D-Ala-Gly-Phe-Leu (Pentapeptide-18) or a derivative thereof a second polypeptide comprising the sequence Ac-Glu-Glu-Met-Gln-Arg-Arg-CONH$_2$ (Acetyl Hexapeptide-8) (SEQ ID NO: 4) or a derivative thereof; a third polypeptide comprising Pal-Gly-Gln-Pro-Arg (Palmitoyl Tetrapeptide-7) (SEQ ID NO: 7) or a derivative thereof; and a fourth polypeptide comprising the sequence Ac-beta-Ala-His-Ser-His (Acetyl Tetrapeptide-5) (SEQ ID NO: 5) or a derivative thereof.

In some cases is a method of reducing the depth of wrinkles on the skin of a subject, comprising providing to the subject a composition for cosmetic use described herein in an amount and time sufficient for reducing the depth of wrinkles on the skin of said subject.

In some cases is a method of brightening the skin tone of a subject, comprising providing to the subject a composition for cosmetic use described herein in an amount and time sufficient for brightening the skin tone of said subject.

Provided herein is a composition for cosmetic use comprising: at least one neolignan; at least one molecule of Formula I; and at least one ultraviolet spectrum attenuating agent comprising a plurality of nanoparticles or microparticles. In some cases, the molecule of Formula I is ergothioneine. The neolignan may be honokiol. In some cases, the at least one ultraviolet spectrum attenuating agent comprises zinc oxide, titanium dioxide, derivatives or combinations thereof. The composition may also comprise a plurality of hyaluronic microspheres.

Provided is a composition for cosmetic use, comprising ergothioneine; honokiol; ectoin; zinc oxide; titanium dioxide; hyaluronic acid or a salt thereof. In some cases, the composition comprises sodium hyaluronate.

Provided is a method of reducing the appearance of fine lines on the skin of a subject comprising providing to said subject a composition for cosmetic use described herein, in an amount and time sufficient for reducing the appearance of fine lines on the skin of said subject.

In methods provided herein, the subject maybe a human. In some cases, the subject maybe a human in need of the methods described herein.

In some cases, in compositions and methods described herein the honokiol is provided in the form of *magnolia* bark extract. The *magnolia* bark extract may be in liposomal form. In some cases, compositions described herein comprise about 0.01% w/w-25% w/w *magnolia* bark extract, 0.1% w/w-70% w/w ergothioneine, and 0.1 w/w-25% w/w ectoin, based on the total weight of the composition.

Composition described herein may be in the form of at least one of a cream, lotion, serum, gel and moisturizer. Compositions described herein may further comprise at least one of Vitamin C Ester, Peptide Blends, Alpha Hydroxy and Beta Hydroxy Acids, Mushroom Ferment Extract, Multi-mineral Blends, Phospholipids, Caffeine, and Micro-Algae Blends.

Provided is a composition comprising cyclopentasiloxane, C12-15 Alkyl Benzoate, Titanium Dioxide, Zinc Oxide, Dimethicone, Polyglyceryl-3 Polydimethylsiloxyethyl Dimethicone, Dimethicone/PEG-10/15 Crosspolymer, Stearic Acid, Aluminum Hydroxide, Sodium Chloride, Glycerin, *Magnolia Officinalis* Bark Extract, Ectoin, Caprylyl Glycol, Teprenone, Sodium Hyaluronate, *Vitis Vinifera* (Grape) Seed Extract, Tetrahexyldecyl Ascorbate, Ergothioneine, Tocopheryl Acetate, Tocopherol, Maltodextrin, Lecithin, Ethylhexyl Palmitate, Caprylic/Capric Triglyceride, PEG/PPG-18/18 Dimethicone, Polyglycerin-3 Crosspolymer, Hexyl Laurate, Cyclohexasiloxane, Triethoxysilylethyl Polydimethylsiloxyethyl Hexyl Dimethicone, Dimethicone/Vinyl Dimethicone Crosspolymer, Polyglyceryl-4 Isostearate, Cetyl PEG/PPG-10/1 Dimethicone, Silica Dimethyl Silylate, Triethoxycaprylylsilane, Phenoxyethanol, Ethylhexylglycerin, Butylene Glycol, Hexylene Glycol, Fragrance, Mica and Silica.

In some embodiments is a composition, wherein said composition comprises Potassium Azeloyl Diglycinate, *Hamamelis Virginiana* (Witch Hazel) Extract, Glycerin, Methyl Gluceth-20, *Magnolia Officinalis* Bark Extract, Ergothioneine, Ectoin, Pentylene Glycol, *Salix Nigra* (Willow) Bark Extract, Magnesium Aspartate, Zinc Gluconate, Copper Gluconate, *Microcitrus Austraiasica* Fruit Extract, *Mucor Miehei* Extract, Glucosamine HCl, Urea, Phenoxyethanol, Ethylhexylglycerin, Polysorbate 20, *Magnolia Glauca* Flower Water, Sodium PCA, Potassium Sorbate, Allantoin, Dipotassium Glycyrrhizate, Alcohol Denatured, Disodium EDTA, Lactic Acid, Maltodextrin, Lecithin, Tocopherol, *Vitis Vinifera* (Grape) Seed Extract, Sodium Hydroxide, Caprylic/Capric Triglyceride, *Jasminum Officinale* (Jasmine) Extract, Rosa *Damascena* Flower Oil, *Pelargonium Graveolens* Oil, *Citrus Medica* Limonum (Lemon) Peel Oil, *Camellia Sinensis* Leaf (Green Tea) Extract, Mentha *Viridis* (Spearmint) Leaf Oil, and *Juniperus Virginiana* Oil.

In some embodiments is a composition, wherein said composition comprises Glycerin, *Ricinus Communis* (Castor) Seed Oil, Cetearyl Olivate, Lecithin, Caprylic/Capric Triglyceride, Sorbitan Olivate, Cetearyl Alcohol, Dimethicone, Ergothioneine, Isosorbide Dicaprylate, Glyceryl Behenate, Ethyl Linoleate, Ethylhexyl Palmitate, Silica Dimethyl Silylate, Butylene Glycol, Sodium Hyaluronate, *Magnolia Officinalis* Bark Extract, Ectoin, Tetrahexyldecyl Ascorbate, Panthenol, Hydrogenated Castor Oil, Cera Alba, Copernicia Cerifera (Carnauba) Wax, Sodium PCA, Urea, Trehalose, Triacetin, Polyquaternium-51, Methylglucoside Phosphate, Copper Lysinate/Prolinate, Ceteareth-20, Magnesium Aspartate, Zinc Gluconate, Copper Gluconate, C8-22 Alkyl Acrylates/Methacrylic Acid Crosspolymer, *Persea Gratissima* (Avocado) Oil, Squalane, *Oenothera Biennis* (Evening Primrose) Oil, Fragrance, Allantoin, Stearyl Glycyrrhetinate, Maltodextrin, Tocopherol, *Vitis Vinifera* (Grape) Seed Extract, Xanthan Gum, Arginine, Aloe Barbadensis Leaf Juice, *Macadamia Ternifolia* Seed Oil, Phenoxyethanol, Ethylhexylglycerin, Sodium Phytate, and *Tricholoma* Matsutake Extract.

In some embodiments is a composition, wherein said composition comprises Pentapeptide-18, Acetyl Hexapeptide-8, Caprylyl Methicone, Glycerin, Butylene Glycol, Beta Glucan (Oat), Isosorbide Dicaprylate, Dimethicone, Isostearyl Alcohol, Butylene Glycol Cocoate, Polyacrylate-13, *Magnolia Officinalis* Bark Extract, Ergothioneine, Ectoin, Palmitoyl Tetrapeptide-7, Acetyl Tetrapeptide-5, Tetrahexyldecyl Ascorbate, Tyrosine, Hesperidin Methyl Chalcone, *Tricholoma* Matsutake Extract, Corallina *Officinalis* Extract, Sodium Hyaluronate, Sodium Potassium Aluminum Silicate, Silica, Pullulan, Steareth-20, Dipeptide-2, Ethylcellulose, Polysorbate 20, Polyisobutene, Dimethiconol, Panthenol, *Oryza Sativa* (Rice) Bran Oil, Lecithin, Allantoin, Xanthan Gum, *Elaeis Guineensis* Oil, Tocotrienols, Tocopherol, Phenoxyethanol, Maltodextrin, *Vitis Vinifera* (Grape) Seed Extract, Sodium Phytate, Fragrance, Ethylhexylglycerin, Mica, and Titanium Dioxide.

In some embodiments is an article of manufacture comprising a peel pad and a composition described herein. In some cases, the peel pad comprises a composition described herein adsorbed or absorbed upon it. In some cases is the facial pad, wherein said pad comprises Potassium Azeloyl Diglycinate, *Hamamelis Virginiana* (Witch Hazel) Extract, Glycerin, Methyl Gluceth-20, *Magnolia Officinalis* Bark Extract, Ergothioneine, Ectoin, Pentylene Glycol, *Salix Nigra* (Willow) Bark Extract, Magnesium Aspartate, Zinc Gluconate, Copper Gluconate, *Microcitrus Austraiasica* Fruit Extract, *Mucor Miehei* Extract, Glucosamine HCl, Urea, Phenoxyethanol, Ethylhexylglycerin, Polysorbate 20, *Magnolia Glauca* Flower Water, Sodium PCA, Potassium Sorbate, Allantoin, Dipotassium Glycyrrhizate, Alcohol Denatured, Disodium EDTA, Lactic Acid, Maltodextrin, Lecithin, Tocopherol, *Vitis Vinifera* (Grape) Seed Extract, Sodium Hydroxide, Caprylic/Capric Triglyceride, *Jasminum Officinale* (Jasmine) Extract, Rosa *Damascena* Flower Oil, *Pelargonium Graveolens* Oil, *Citrus Medica* Limonum (Lemon) Peel Oil, *Camellia Sinensis* Leaf (Green Tea) Extract, Mentha *Viridis* (Spearmint) Leaf Oil, and *Juniperus Virginiana* Oil.

Provided is a method of reducing the visible signs of skin aging, including: exfoliating the skin with a composition described herein; treating the skin with a composition described herein; and/or moisturizing the skin with a composition described herein. In some cases, the exfoliating, treating and/or moisturizing may be repeated two, three, four, or five times daily. In some cases, the exfoliating, treating and/or moisturizing may be repeated two, three, four, or five times on alternate days. In some cases, the exfoliating, treating and/or moisturizing may be repeated for about 10, about 15, about 20, about 25, about 30, about 45, about 50, about 60, about 70, about 75, or about 90 days.

In some embodiments, is a composition described herein, wherein the composition is an antioxidant composition. In some cases, the composition comprises at least two ingredients which provide synergistic antioxidant effect. In certain embodiments, the synergistic antioxidant effect is studied by exposing HaCaT cells to said composition, followed by exposing said cells to TBHP.

In some embodiments is a method of making a composition comprising combining: at least one neolignan; ectoin; and a molecule of Formula I. In some cases, the molecule of Formula I is EGT. In some cases is the method further comprising at least one ingredient selected from the group consisting of: Potassium Azeloyl Diglycinate, *Hamamelis Virginiana* (Witch Hazel) Extract, Glycerin, Methyl Gluceth-20, *Magnolia Officinalis* Bark Extract, Pentylene Glycol, *Salix Nigra* (Willow) Bark Extract, Magnesium Aspartate, Zinc Gluconate, Copper Gluconate, *Microcitrus Austraiasica* Fruit Extract, *Mucor Miehei* Extract, Glucosamine HCl, Urea, Phenoxyethanol, Ethylhexylglycerin, Polysorbate 20, *Magnolia Glauca* Flower Water, Sodium PCA, Potassium Sorbate, Allantoin, Dipotassium Glycyrrhizate, Alcohol Denatured, Disodium EDTA, Lactic Acid, Maltodextrin, Lecithin, Tocopherol, *Vitis Vinifera* (Grape) Seed Extract, Sodium Hydroxide, Caprylic/Capric Triglyceride, *Jasminum Officinale* (Jasmine) Extract, *Rosa Damascena* Flower Oil, *Pelargonium Graveolens* Oil, *Citrus Medica* Limonum (Lemon) Peel Oil, *Camellia Sinensis* Leaf (Green Tea) Extract, Mentha *Viridis* (Spearmint) Leaf Oil, *Juniperus Virginiana* Oil, Pentapeptide-18, Acetyl Hexapeptide-8, Caprylyl Methicone, Glycerin, Butylene Glycol, Beta Glucan (Oat), Isosorbide Dicaprylate, Dimethicone, Isostearyl Alcohol, Butylene Glycol Cocoate, Polyacrylate-13, *Magnolia Officinalis* Bark Extract, Ergothioneine, Ectoin, Palmitoyl Tetrapeptide-7, Acetyl Tetrapeptide-5, Tetrahexyldecyl Ascorbate, Tyrosine, Hesperidin Methyl Chalcone, *Tricholoma Matsutake* Extract, *Corallina Officinalis* Extract, Sodium Hyaluronate, Sodium Potassium Aluminum Silicate, Silica, Pullulan, Steareth-20, Dipeptide-2, Ethylcellulose, Polysorbate 20, Polyisobutene, Dimethiconol, Panthenol, *Oryza Sativa* (Rice) Bran Oil, Lecithin, Allantoin, Xanthan Gum, *Elaeis Guineensis* Oil, Tocotrienols, Tocopherol, Phenoxyethanol, Maltodextrin, *Vitis Vinifera* (Grape) Seed Extract, Sodium Phytate, Fragrance, Ethylhexylglycerin, Mica, Titanium Dioxide, Glycerin, *Ricinus Communis* (Castor) Seed Oil, Cetearyl Olivate, Lecithin, Caprylic/Capric Triglyceride, Sorbitan Olivate, Cetearyl Alcohol, Dimethicone, Ergothioneine, Isosorbide Dicaprylate, Glyceryl Behenate, Ethyl Linoleate, Ethylhexyl Palmitate, Silica Dimethyl Silylate, Butylene Glycol, Sodium Hyaluronate, *Magnolia Officinalis* Bark Extract, Ectoin, Tetrahexyldecyl Ascorbate, Panthenol, Hydrogenated Castor Oil, Cera Alba, Copernicia Cerifera (Carnauba) Wax, Sodium PCA, Urea, Trehalose, Triacetin, Polyquaternium-51, Methylglucoside Phosphate, Copper Lysinate/Prolinate, Ceteareth-20, Magnesium Aspartate, Zinc Gluconate, Copper Gluconate, C8-22 Alkyl Acrylates/Methacrylic Acid Crosspolymer, *Persea Gratissima* (Avocado) Oil, Squalane, *Oenothera Biennis* (Evening Primrose) Oil, Fragrance, Allantoin, Stearyl Glycyrrhetinate, Maltodextrin, Tocopherol, *Vitis Vinifera* (Grape) Seed Extract, Xanthan Gum, Arginine, Aloe Barbadensis Leaf Juice, *Macadamia Ternifolia* Seed Oil, Phenoxyethanol, Ethylhexylglycerin, Sodium Phytate, *Tricholoma Matsutake* Extract, cyclopentasiloxane, C12-15 Alkyl Benzoate, Titanium Dioxide, Zinc Oxide, Dimethicone, Polyglyceryl-3 Polydimethylsiloxyethyl Dimethicone, Dimethicone/PEG-10/15 Crosspolymer, Stearic Acid, Aluminum Hydroxide, Sodium Chloride, Glycerin, *Magnolia Officinalis* Bark Extract, Ectoin, Caprylyl Glycol, Teprenone, Sodium Hyaluronate, Tetrahexyldecyl Ascorbate, Ergothioneine, Tocopheryl Acetate, Tocopherol, Maltodextrin, Lecithin, Ethylhexyl Palmitate, Caprylic/Capric Triglyceride, PEG/PPG-18/18 Dimethicone, Polyglycerin-3 Crosspolymer, Hexyl Laurate, Cyclohexasiloxane, Triethoxysilylethyl Polydimethylsiloxyethyl Hexyl Dimethicone, Dimethicone/Vinyl Dimethicone Crosspolymer, Polyglyceryl-4 Isostearate, Cetyl PEG/PPG-10/1 Dimethicone, Silica Dimethyl Silylate, Triethoxycaprylylsilane, Phenoxyethanol, Ethylhexylglycerin, Butylene Glycol, Hexylene Glycol, Fragrance, Mica and Silica. In some cases, the composition is in the form of at least one selected from the group consisting of a cream, lotion, serum, gel and moisturizer.

Provided is a kit comprising a composition described herein, and at least one container. A kit may further comprise instructions for use. In some cases is provided a system comprising at least two kits described herein. In some cases, at least two of the at least two kits are different It is understood that the examples and embodiments described herein are for illustrative purposes only and that various modifications or changes in light thereof will be suggested to persons skilled in the art and are to be included within the spirit and purview of this application and scope of the appended claims.

EXAMPLES

It is understood that the examples and embodiments described herein are for illustrative purposes only and that various modifications or changes in light thereof will be suggested to persons skilled in the art and are to be included within the spirit and purview of this application and scope of the appended claims.

The reagents employed in the examples are commercially available or can be prepared using commercially available instrumentation, methods, or reagents known in the art. The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

Example 1

Clinical Evaluation of Compositions Provided Herein

Evaluation

Benefits of the compositions described herein are evaluated in a controlled, independent single-blind study using advanced imaging technology, overseen by a dermatologist. The goal is to evaluate at least one of the top 10 visible signs of aging—lines and wrinkles, loss of elasticity (firmness), spots and pigmentation, redness, loss of radiance, uneven skin texture (roughness), loss of moisture, sallowness (dull skin), dehydration, and thin skin.

Methods

A six-week clinical efficacy trial is performed on the compositions provided herein with a third party testing facility using advanced imaging technology. The testing facility randomly recruits female subjects between 35 and 60 years who have no knowledge of the product details and who use the compositions described herein twice daily per our standard directions for use. Participants complete a "washout" period before starting the method and refrain from using any other facial skincare treatments including retinoids, AHA products, exfoliating scrubs or Clarisonic devices other than the methods and compositions described herein:

STEP 1: Cleansing using a composition provided herein.
STEP 2: Peel Pads comprising a composition provided herein.
STEP 3: Serum comprising a composition provided herein.
STEP 4 (AM): Moisturizer SPF 20 comprising a composition provided herein.
STEP 4 (PM): Moisture Injection Cream comprising a composition provided herein.

Analysis includes standard white light, cross-polarized and UV lighting to record and measure surface and subsurface skin conditions. UV photography provides the most complete data set available for sun damage assessment and analysis, including UV fluorescence imaging. At baseline and after 4 and 6 weeks of product use, a trained technician takes digital images of the face of each subject. Using ImagePro® software, the images are analyzed to determine changes in the depth of global facial wrinkles, skin radiance/luminosity and skin lightness.

Clinical Results

Global Facial Wrinkles

Digital images are analyzed to determine improvement in the depth of global facial wrinkles.

Skin Radiance/Luminosity

Digital images are analyzed to determine improvement in skin radiance/luminosity.

Skin Lightness

Digital images are analyzed to determine improvement in skin lightness.

Consumer Perception Results

In the same panel of female subjects, aged 35-60 years, after 4 and 6 weeks of product use, subjects are asked to report on the appearance of their skin including improvement in the overall appearance of skin texture; feeling more hydrated; improvement in skin's overall appearance; feeling more moisturized; feeling firmer; appearing more radiant; having a healthier glow; improvement in resilience/feel in the elasticity of their skin; observing less visible redness after using the methods and compositions described herein.

Example 2

Clinical Evaluation of Specific Compositions Provided Herein

Evaluation

Benefits of the compositions described herein were evaluated in a controlled, independent single-blind study using advanced imaging technology, overseen by a dermatologist. The goal was to evaluate one or more visible signs of aging, for instance: lines and wrinkles, loss of elasticity (firmness), spots and pigmentation, redness, loss of radiance, uneven skin texture (roughness), loss of moisture, sallowness (dull skin), dehydration, and thin skin.

Compositions Included in the Study:

Cleansing Balm: Ingredients included *Sesamum Indicum* (Sesame) Seed Oil, Oleic Acid, Oleth-20, Trihydroxystearin, Polyglyceryl-3 Diisostearate, Glyceryl Monostearate, *Prunus Domestica* Seed Oil, Cera Alba, Linoleic Acid, Silica, Water, Stearyl Glycyrrhetinate, Linolenic Acid, Ascorbyl Palmitate, Tetrahexyldecyl Ascorbate, Bisabolol, Tocotrienols, Tocopheryl Acetate, Stearic Acid, Glycerin, Tocopherol, Maltodextrin, Squalene, Beta-Glucan, Palmitic Acid, Phenoxyethanol, Dehydroacetic Acid, Benzoic Acid, Ethylhexylglycerin, and Fragrance.

Peel Pads: Ingredients included Water, Potassium Azeloyl Diglycinate, *Hamamelis Virginiana* (Witch Hazel) Extract, Glycerin, Methyl Gluceth-20, *Magnolia Officinalis* Bark Extract, Ergothioneine, Ectoin, Pentylene Glycol, *Salix Nigra* (Willow) Bark Extract, Magnesium Aspartate, Zinc Gluconate, Copper Gluconate, *Microcitrus Austraiasica* Fruit Extract, *Mucor Miehei* Extract, Glucosamine HCl, Urea, Phenoxyethanol, Ethylhexylglycerin, Polysorbate 20, *Magnolia Glauca* Flower Water, Sodium PCA, Potassium Sorbate, Allantoin, Dipotassium Glycyrrhizate, Alcohol Denatured, Disodium EDTA, Lactic Acid, Maltodextrin, Lecithin, Tocopherol, *Vitis Vinifera* (Grape) Seed Extract, Sodium Hydroxide, Caprylic/Capric Triglyceride, *Jasminum Officinale* (Jasmine) Extract, *Rosa Damascena* Flower Oil, *Pelargonium Graveolens* Oil, *Citrus Medica* Limonum (Lemon) Peel Oil, *Camellia Sinensis* Leaf (Green Tea) Extract, Mentha *Viridis* (Spearmint) Leaf Oil, and *Juniperus Virginiana* Oil.

Quattro-Peptide Face and Eye Serum: Ingredients included Water, Pentapeptide-18, Acetyl Hexapeptide-8, Caprylyl Methicone, Glycerin, Butylene Glycol, Beta Glucan (Oat), Isosorbide Dicaprylate, Dimethicone, Isostearyl Alcohol, Butylene Glycol Cocoate, Polyacrylate-13, *Magnolia Officinalis* Bark Extract, Ergothioneine, Ectoin, Palmitoyl Tetrapeptide-7, Acetyl Tetrapeptide-5, Tetrahexyldecyl Ascorbate, Tyrosine, Hesperidin Methyl Chalcone, *Tricholoma Matsutake* Extract, *Corallina Officinalis* Extract, Sodium Hyaluronate, Sodium Potassium Aluminum Silicate, Silica, Pullulan, Steareth-20, Dipeptide-2, Ethylcellulose, Polysorbate 20, Polyisobutene, Dimethiconol, Panthenol, *Oryza Sativa* (Rice) Bran Oil, Lecithin, Allantoin, Xanthan Gum, *Elaeis Guineensis* Oil, Tocotrienols, Tocopherol, Phenoxyethanol, Maltodextrin, *Vitis Vinifera* (Grape) Seed Extract, Sodium Phytate, Fragrance, Ethylhexylglycerin, Mica, and Titanium Dioxide.

Moisturizer SPF 20: Ingredients included Titanium Dioxide 1%. Zinc Oxide 10%. Inactive Ingredients: Water, Caprylic/Capric Triglyceride, Glyceryl Stearate, Ergothioneine, Cetyl Alcohol, Dimethicone, Phenyl Trimethicone, Glycerin, Ethylhexyl Palmitate, *Magnolia Officinalis* Bark Extract, Ectoin, Palmitoyl Hexapeptide-19, Tocopherol, Sodium Hyaluronate, *Vitis Vinifera* (Grape) Seed Extract, Sodium PCA, Lecithin, Jojoba Esters, Phytic Acid, Cetearyl Alcohol, Caprylyl Glycol, Hydrogenated Lecithin, Citric Acid, Tetrahexyldecyl Ascorbate, Polyacrylamide, Silica, Xanthan Gum, Ceteareth-20, C13-14 Isoparaffin, Glyceryl Isostearate, Polyhydroxystearic Acid, Glyceryl Polyacrylate, Maltodextrin, Hydroxyethyl Acrylate/Sodium Acryloyl Dimethyl, Taurate Copolymer, Laureth 7, Silica Dimethyl Silylate, Butylene Glycol, Pentylene Glycol, Polysorbate 20, PEG-100 Stearate, Fragrance, Phenoxyethanol, Iron Oxides, Mica, and Tin Oxide.

Moisture Injection Cream: Ingredients included Water, Glycerin, *Ricinus Communis* (Castor) Seed Oil, Cetearyl Olivate, Lecithin, Caprylic/Capric Triglyceride, Sorbitan Olivate, Cetearyl Alcohol, Dimethicone, Ergothioneine, Isosorbide Dicaprylate, Glyceryl Behenate, Ethyl Linoleate, Ethylhexyl Palmitate, Silica Dimethyl Silylate, Butylene Glycol, Sodium Hyaluronate, *Magnolia Officinalis* Bark Extract, Ectoin, Tetrahexyldecyl Ascorbate, Panthenol, Hydrogenated Castor Oil, Cera Alba, *Copernicia Cerifera* (Carnauba) Wax, Sodium PCA, Urea, Trehalose, Triacetin, Polyquaternium-51, Methylglucoside Phosphate, Copper Lysinate/Prolinate, Ceteareth-20, Magnesium Aspartate, Zinc Gluconate, Copper Gluconate, C8-22 Alkyl Acrylates/Methacrylic Acid Crosspolymer, *Persea Gratissima* (Avocado) Oil, Squalane, *Oenothera Biennis* (Evening Primrose) Oil, Fragrance, Allantoin, Stearyl Glycyrrhetinate, Maltodextrin, Tocopherol, *Vitis Vinifera* (Grape) Seed Extract, Xanthan Gum, Arginine, *Aloe Barbadensis* Leaf Juice, *Macadamia Ternifolia* Seed Oil, Phenoxyethanol, Ethylhexylglycerin, Sodium Phytate, and *Tricholoma Matsutake* Extract.

Methods

A six-week clinical efficacy trial was commissioned with a third party testing facility using advanced imaging technology. The testing facility randomly recruited 43 female subjects between 35 and 55 years who had no knowledge of the product details and who used the four steps outlined below, twice daily per our standard directions for use. Participants completed a "wash-out" period before starting the Regimen and refrained from using any other facial skincare treatments including retinoids, AHA products, exfoliating scrubs or Clarisonic devices other than the compositions used in this example.

STEP 1: Cleansing Balm.
STEP 2: Peel Pads.
STEP 3: Quattro-Peptide Face and Eye Serum.
STEP 4 (AM): Moisturizer SPF 20.
STEP 4 (PM): Moisture Injection Cream.

The analysis included standard white light, cross-polarized and UV lighting to record and measure surface and subsurface skin conditions. UV photography provides the most complete data set available for sun damage assessment and analysis, including UV fluorescence imaging. At baseline and after 4 and 6 weeks of product use, a trained technician took digital images of the face of each subject. Using ImagePro® software, the images were analyzed to determine changes in the depth of global facial wrinkles, skin radiance/luminosity and skin lightness.

Clinical Results

Global Facial Wrinkles

Digital images were analyzed to determine improvement in the depth of visible, global facial wrinkles. All of the improvements observed were statistically significant when compared with baseline. A total of 74% and 88% of the subjects showed improvement in visible, global facial wrinkles after 4 and 6 weeks, respectively.

Skin Radiance/Luminosity

Digital images were analyzed to determine improvement in skin radiance/luminosity. All of the improvements observed were statistically significant when compared with baseline. A total of 63% and 77% of the subjects showed improvement in skin radiance/luminosity after 4 and 6 weeks, respectively.

Skin Lightness

Digital images were analyzed to determine improvement in skin lightness. All of the improvements observed were statistically significant when compared with baseline. A total of 72% and 77% of the subjects showed improvement in skin lightness after 4 and 6 weeks, respectively.

Consumer Perception Results

In the same panel of 43 female subjects, aged 35-55 years, after 4 and 6 weeks of product use, subjects were asked to report on the appearance of their skin.

At 4 Weeks:

100% reported an improvement in the overall appearance of skin texture.
98% reported their skin feels more hydrated.
98% reported an improvement in skin's overall appearance.
93% reported their skin feels more moisturized.
91% reported their skin feels firmer.
88% reported their skin appears more radiant.
88% reported their skin has a healthier glow.
86% reported an improvement in resilience/feel in the elasticity of their skin.

In those women who had skin redness before using the regime (N=29) 80% believed their skin appeared less red after using the regime.

In the same panel of 43 female subjects, aged 35-55 years, after 6 weeks of product use, subjects were asked to report on the appearance of their skin.

At 6 Weeks:

100% reported their skin feels more hydrated and moisturized.

98% reported their skin has a healthier glow.

96% said they would recommend the regimen to their friends and family.

95% reported an improvement in skin's overall appearance.

93% reported an improvement in resilience/feel in the elasticity of the skin.

93% believe their skin feels firmer.

86% reported an improvement in the look of fine lines on the face.

86% reported that the Peel Pads worked without the irritation of other peel products (of those who have used peel pads in the past).

79% reported they would purchase this system if available and at a reasonable price.

76% reported an improvement in the appearance of skin hyperpigmentation (dark spots, age spots, discoloration).

74% reported a reduction in the look of "crows feet" (fine lines at the outside corners of the eyes).

Example 3

30 Day Clinical Evaluation of Compositions Provided Herein

Evaluation

Benefits of the compositions described herein were evaluated in an extended study over 30 days. The goal was to evaluate one or more visible signs of aging, e.g. lines and wrinkles, loss of elasticity (firmness), spots and pigmentation, redness, loss of radiance, uneven skin texture (roughness), loss of moisture, sallowness (dull skin), dehydration, and thin skin. The study was performed in a control group of 17 women and 1 man, aged 35-55, with skin ranging from normal to dry, aging skin. Subjects used the compositions provided in Example 2.

Quantitative Data

100% said they see an improvement in skin's overall appearance.

95% said skin feels more moisturized.

95% said their skin appears more radiant.

95% said the experience of using the regimen is simple, easy and fun.

95% said skin has a healthier glow.

94% agree they noticed a difference in just 30 days.

89% saw/felt a noticeable glow after 30 days.

83% said their skin is noticeably softer after 30 days of using the regimen.

83% said their skin feels firmer.

78% said they see an improvement in the appearance of skin hyperpigmentation (dark spots, age spots).

78% said they notice an improvement in visible fine lines and wrinkles on the face.

78% really saw results from these products versus other products they've used.

77% said their skin is noticeably smoother after just 30 days of using the regimen.

72% saw/felt an immediate improvement in their skin each time they use the regimen.

72% noticed an improvement in skin's elasticity.

61% noticed a reduction in pore size or number of pores.

60% noticed a reduction in the appearance of skin redness.

55% pores appeared less clogged.

50% reported these products worked better than products than they have received from dermatologists or doctors.

47% noticed a reduction in the depths of visible wrinkles and fine lines.

44% said they notice a reduction in fine lines at the outside corners of the eyes.

36% noticed a reduction in the appearance of blemishes and breakouts.

Example 4

Anti-oxidant Study

Assay Information:

Test System: Human Keratinocytes, e.g. spontaneously transformed aneuploid immortal keratinocyte cell line from adult human skin (HaCaT).

96-well plates of HaCaT cells are used for the study. At least one plate is pre-loaded with DCFDA for 30 minutes prior to treatment. The second plate, used to assess glutathione (GSH) depletion, is not pre-treated in any way. After DCFDA solution is removed, treatments with antioxidants begin. After 1 hour, antioxidant treatment media is removed. Generation of reactive oxygen species is induced by applying tert-butylhydroperoxide (TBHP) to the cells at a concentration of 1% (v/v). Samples are treated in three ways: Group A receives phosphate buffered saline (no TBHP), Group B receives 1% TBHP, and Group C is pretreated with compositions provided herein followed by treatment oxidant 1% TBHP. Historic data has shown that 1 hour is sufficient to elicit DCFDA fluorescence and GSH depletion; however cells treated with DCFDA can be read at 1, 3, 6 and 24 hours post-peroxide dose to assess oxidative stress. After exposure total glutathione and leakage of lactate dehydrogenase (LDH) (a general cytotoxicity marker) is assessed. Compositions provided herein are tested individually and in combination. The antioxidant properties of the compositions are determined by comparing the response to the pro-oxidant in Group B to the response of the antioxidant plus pro-oxidant in group C.

The compositions provided herein have an antioxidant effect that is greater than the antioxidant effect of each ingredient taken separately. In some cases, the antioxidant effect of a composition provided herein is greater than the expected additive antioxidant effect of each of the ingredients.

Example 5

Stability Testing

A composition described herein containing at least one of neolignan, ectoin, and the molecule of Formula I is placed sideways in a 25° C.±2° C./60% Relative Humidity (RH) ±5% Relative Humidity (RH) environmental storage chamber for different intervals to yield a period of 6 months and in a 40° C.±2° C./75% RH±5% RH environmental storage chamber for different intervals to yield a period of 6 months. The data collected from these studies reflect the performance and the behavior of this product per ICH Guidelines to yield a 2 year shelf life.

While specific embodiments of the present invention have been shown and described herein, those skilled in the art would understand that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising:
   at least one neolignan;
   ectoin; and
   a molecule of Formula I:

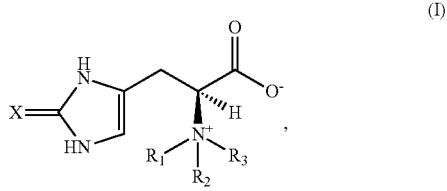

(I)

wherein $R_1$, $R_2$ and $R_3$ are independently H, methyl, ethyl, propyl, or isopropyl;
wherein X is S or O;
wherein said composition when contacted with a skin cell in a predetermined amount for a predetermined period of time results in a reduction of at least one symptom of skin aging.

2. The composition of claim 1, wherein said at least one neolignan is honokiol provided in the form of *magnolia* bark extract or a derivative thereof.

3. The composition of claim 1, further comprising at least one ultraviolet spectrum attenuating agent comprising zinc oxide, titanium dioxide, derivatives or combinations thereof, in an amount sufficient to reduce the exposure of said skin cell from ultraviolet radiation as compared to an otherwise identical composition not comprising said ultraviolet spectrum attenuating agent.

4. The composition of claim 3, comprising from about 1% w/w to about 20% w/w zinc oxide and from about 0.5% w/w to about 20% w/w titanium dioxide based on the total weight of the composition.

5. The composition of claim 1, further comprising at least one polypeptide, derivative or fragment thereof; or protein, derivative or fragment thereof.

6. The composition of claim 5, comprising at least one polypeptide, wherein said at least one polypeptide comprises the sequence: Tyr-D-Ala-Gly-Phe-Leu.

7. The composition of claim 5, comprising at least one polypeptide, wherein said at least one polypeptide comprises the sequence Glu-Glu-Met-Gln-Arg-Arg (SEQ ID NO: 1).

8. The composition of claim 5, comprising a palmitic acid conjugate of a polypeptide comprising the sequence Gly-Gln-Pro-Arg (SEQ ID NO: 2).

9. The composition of claim 5, comprising at least one polypeptide, wherein said at least one polypeptide comprises the sequence beta-Ala-His-Ser-His (SEQ ID NO: 3), or a derivative thereof.

10. The composition of claim 1, further comprising:

a first polypeptide comprising the sequence Tyr-D-Ala-Gly-Phe-Leu (Pentapeptide-18) or a derivative thereof;

a second polypeptide comprising the sequence Ac-Glu-Glu-Met-Gln-Arg-Arg-CONH$_2$ (Acetyl Hexapeptide-8) (SEQ ID NO: 4) or a derivative thereof;

a third polypeptide which is a palmitic acid conjugate of a polypeptide comprising the sequence Gly-Gln-Pro-Arg (Palmitoyl Tetrapeptide-7) (SEQ ID NO: 2) or a derivative thereof; and a fourth polypeptide comprising the sequence Ac-beta-Ala-His-Ser-His (Acetyl Tetrapeptide-5) (SEQ ID NO: 5) or a derivative thereof.

11. The composition of claim 1, wherein said reduction of at least one symptom of skin aging is selected from the group consisting of:

an improvement in the appearance of skin hyperpigmentation;

a reduction in the appearance of crow's feet;

an improvement in the elasticity of the skin;

an improvement in the firmness or texture of the skin; and a reduction in the appearance of redness of the skin.

12. The composition of claim 1, wherein said predetermined period of time is from about one day to about 24 weeks.

13. The composition of claim 1, comprising about 0.01% w/w-25% w/w neolignan, 0.1% w/w-70% w/w molecule of Formula I, and 0.1 w/w-25% w/w ectoin based on the total weight of the composition.

14. A composition, comprising ergothioneine;

honokiol;

ectoin;

a first polypeptide comprising the sequence Tyr-D-Ala-Gly-Phe-Leu (Pentapeptide-18) or a derivative thereof;

a second polypeptide comprising the sequence Ac-Glu-Glu-Met-Gln-Arg-Arg-CONH$_2$ (Acetyl Hexapeptide-8) (SEQ ID NO: 4) or a derivative thereof;

a third polypeptide which is a palmitic acid conjugate of a polypeptide comprising the sequence Gly-Gln-Pro-Arg (Palmitoyl Tetrapeptide-7) (SEQ ID NO: 2) or a derivative thereof; and a fourth polypeptide comprising the sequence Ac-beta-Ala-His-Ser-His (Acetyl Tetrapeptide-5) (SEQ ID NO: 5) or a derivative thereof.

15. A method of reducing the depth of visible wrinkles on the skin of a subject comprising contacting the skin of said subject with the composition of claim 14 in an amount and time sufficient for reducing the depth of visible wrinkles on the skin of said subject.

16. A method of making a composition comprising combining:

at least one neolignan;

ectoin;

a molecule of Formula I:

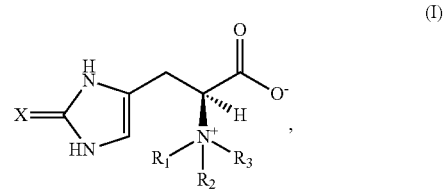

wherein $R_1$, $R_2$ and $R_3$ are independently H, methyl, ethyl, propyl, or isopropyl; and wherein X is S or O; and at least one ingredient selected from the group consisting of: Potassium Azeloyl Diglycinate, *Hamamelis Virginiana* (Witch Hazel) Extract, Glycerin, Methyl Gluceth-20, *Magnolia Officinalis* Bark Extract, Pentylene Glycol, *Salix Nigra* (Willow) Bark Extract, Magnesium Aspartate, Zinc Gluconate, Copper Gluconate, *Microcitrus Austraiasica* Fruit Extract, *Mucor Miehei* Extract, Glucosamine HCI, Urea, Phenoxyethanol, Ethylhexylglycerin, Polysorbate 20, *Magnolia Glauca* Flower Water, Sodium PCA, Potassium Sorbate, Allantoin, Dipotassium Glycyrrhizate, Alcohol Denatured, Disodium EDTA, Lactic Acid, Maltodextrin, Lecithin, Tocopherol, *Vitis Vinifera* (Grape) Seed Extract, Sodium Hydroxide, Caprylic/Capric Triglyceride, *Jasminum Officinale* (Jasmine) Extract, *Rosa Damascena* Flower Oil, *Pelargonium Graveolens* Oil, *Citrus Medica* Limonum (Lemon) Peel Oil, *Camellia Sinensis*Leaf (Green Tea) Extract, *Mentha Viridis* (Spearmint) Leaf Oil, *Juniperus Virginiana* Oil, Pentapeptide-18, Acetyl Hexapeptide-8, Caprylyl Methicone, Glycerin, Butylene Glycol, Beta Glucan (Oat), Isosorbide Dicaprylate, Dimethicone, Isostearyl Alcohol, Butylene Glycol Cocoate, Polyacrylate-13, *Magnolia Officinalis* Bark Extract, Ergothioneine, Ectoin, Palmitoyl Tetrapeptide-7, Acetyl Tetrapeptide-5, Tetrahexyldecyl Ascorbate, Tyrosine, Hesperidin Methyl Chalcone, *Tricholoma Matsutake* Extract, *Corallina Officinalis* Extract, Sodium Hyaluronate, Sodium Potassium Aluminum Silicate, Silica, Pullulan, Steareth-20, Dipeptide-2, Ethylcellulose, Polysorbate 20, Polyisobutene, Dimethiconol, Panthenol, *Oryza Sativa* (Rice) Bran Oil, Lecithin, Allantoin, Xanthan Gum, *Elaeis Guineensis* Oil, Tocotrienols, Tocopherol, Phenoxyethanol, Maltodextrin, *Vitis Vinifera* (Grape) Seed Extract, Sodium Phytate, Fragrance, Ethylhexylglycerin, Mica, Titanium Dioxide, Glycerin, *Ricinus Communis* (Castor) Seed Oil, Cetearyl Olivate, Lecithin, Caprylic/Capric Triglyceride, Sorbitan Olivate, Cetearyl Alcohol, Dimethicone, Ergothioneine, Isosorbide Dicaprylate, Glyceryl Behenate, Ethyl Linoleate, Ethylhexyl Palmitate, Silica Dimethyl Silylate, Butylene Glycol, Sodium Hyaluronate, *Magnolia Officinalis* Bark Extract, Ectoin, Tetrahexyldecyl Ascorbate, Panthenol, Hydrogenated Castor Oil, *Cera Alba, Copernicia Cerifera* (Carnauba) Wax, Sodium PCA, Urea, Trehalose, Triacetin, Polyquaternium-51, Methylglucoside Phosphate, Copper Lysinate/Prolinate, Ceteareth-20, Magnesium Aspartate, Zinc Gluconate, Copper Gluconate, C8-22 Alkyl Acrylates/Methacrylic Acid Crosspolymer, *Persea Gratissima* (Avocado) Oil, Squalane, *Oenothera Biennis* (Evening Primrose) Oil, Fragrance, Allantoin, Stearyl Glycyrrhetinate, Maltodextrin, Tocopherol, *Vitis Vinifera* (Grape) Seed Extract, Xanthan Gum, Arginine, *Aloe Barbadensis* Leaf Juice, *Macadamia Ternifolia* Seed Oil, Phenoxyethanol, Ethylhexylglycerin, Sodium Phytate, *Tricholoma Matsutake* Extract, cyclopentasiloxane, C12-15 Alkyl Benzoate, Titanium Dioxide, Zinc Oxide, Dimethicone, Polyglyceryl-3Polydimethylsiloxyethyl Dimethicone, Dimethicone/PEG-10/15 Crosspolymer, Stearic Acid, Aluminum Hydroxide, Sodium Chloride, Glycerin, *Magnolia Officinalis* Bark Extract, Ectoin, Caprylyl Glycol, Teprenone, Sodium Hyaluronate, Tetrahexyldecyl Ascorbate, Ergothioneine, Tocopheryl Acetate, Tocopherol, Maltodextrin, Lecithin, Ethylhexyl Palmitate, Caprylic/Capric Triglyceride, PEG/PPG-18/18 Dimethicone, Polyglycerin-3 Crosspolymer, Hexyl Laurate, Cyclohexasiloxane, Triethoxysilylethyl Polydimethylsiloxyethyl Hexyl Dimethicone, Dimethicone/Vinyl Dimethicone Crosspolymer, Polyglyceryl-4 Isostearate, Cetyl PEG/PPG-10/1 Dimethicone, Silica Dimethyl Silylate, Triethoxycaprylylsilane, Phenoxyethanol, Ethylhexylglycerin, Butylene Glycol, Hexylene Glycol, Fragrance, Mica and Silica.

17. The method of claim 16, wherein the composition is in the form of at least one selected from the group consisting of a cream, lotion, serum, gel and moisturizer.

18. A kit comprising the composition of claim 1, at least one container, and instructions for use.

19. A system comprising at least two kits of claim 18.

20. The composition of claim 1, wherein when the composition is stored in a sealed container at 25° C. and the container is placed in an atmosphere having 50% relative humidity and an atmospheric pressure of 1 atmosphere, at least 80% of at least one of neolignan, ectoin, and the molecule of Formula I remains after a period of at least about: 6 months, 1 year, 1.5 years, 2 years, 2.5 years or 3 years.

* * * * *